United States Patent
Drexhage et al.

(10) Patent No.: US 6,384,914 B1
(45) Date of Patent: May 7, 2002

(54) METHOD FOR OPTICAL DETECTION OF ANALYTE MOLECULES IN A NATURAL BIOLOGICAL MEDIUM

(76) Inventors: Karl-Heinz Drexhage, Schanzenweg 50, D-57076 Siegen; Jürgen Wolfrum, Südring 2, D-37127 Rosdorf, both of (DE)

( * ) Notice: Subject to any disclaimer, the term of this patent is extended or adjusted under 35 U.S.C. 154(b) by 0 days.

(21) Appl. No.: 09/423,103

(22) PCT Filed: Apr. 8, 1998

(86) PCT No.: PCT/EP98/02054
§ 371 Date: Oct. 29, 1999
§ 102(e) Date: Oct. 29, 1999

(87) PCT Pub. No.: WO98/49542
PCT Pub. Date: Nov. 5, 1998

(30) Foreign Application Priority Data

Apr. 29, 1997 (DE) .......................................... 197 18 016

(51) Int. Cl.⁷ ............................................... G01N 21/64
(52) U.S. Cl. ......................... 356/318; 356/417; 356/39; 250/458.1
(58) Field of Search ................................ 356/317, 318, 356/417, 39; 250/458.1, 461.1, 461.2, 459.1

(56) References Cited

U.S. PATENT DOCUMENTS 5,348,018 A * 9/1994 Alfano et al.

FOREIGN PATENT DOCUMENTS

EP 0563998 A1 * 10/1993
WO WO 88/07670 * 10/1988

OTHER PUBLICATIONS

Muller et al: "Time–resolved identification of single molecules in solution with a pulsed semiconductor diode laser" Chemical Physics Letters, vol. 262, No. 6, Nov. 29, 1996, pp. 716–722.*

Kollner et al: "Fluorescence pattern recognition for ultrasensitive molecule identification: comparison of experimental data and theoretical approximations", Chemical Physics Letters, vol. 250, No. 3–4, Mar. 1, 1996, pp. 355–360.*

Sauer et al; "Diode laser based detection of single molecules in solutions" Chemical Physics Letters, vol. 254, No. 3–4, May 24, 1996.*

Schneckenburger: "Time resolved microfluorescence in biomedical diagnosis", Optical Engineering, vol. 24, No. 6, Nov. 1985, pp. 1042–1044.*

* cited by examiner

Primary Examiner—F. L. Evans
(74) Attorney, Agent, or Firm—Blakely Sokoloff Taylor & Zafman

(57) ABSTRACT

In order to carry out optical detection and identification of individual tumor markers in undiluted blood plasma, said tumor markers are marked with fluorescent dyes which are characterized by specific fluorescent lifetimes ranging from 0.5 to 6. The blood plasma is exposed to pulsed diode laser radiation emitted in the 630 to 670 nm wavelength range. The emission wavelengths of the dyes are selected in such a way that they are 10 to 60 nm longer than the wavelength of the diode laser. Blood plasma decay curves are detected using time-correlated single photon counts. Said curves are described by a bi-exponential model wherein it is assumed that a fixed fluorescent lifetime for blood plasma emission is 300 ps and that the marked tumor markers have a variable fluorescent lifetime. The relative amount of fluorescent photons in the marked tumors is determined in relation to the overall number of photons detected. If this value exceeds 0.3, a tumor marker is present in the observed volume. The tumor markers can also be identified by the lifetimes which are determined through bi-exponential evaluation. In this manner, individual tumor markers can be detected and identified in undiluted blood plasma.

5 Claims, 5 Drawing Sheets

METHOD FOR OPTICAL DETECTION OF ANALYTE MOLECULES IN A NATURAL BIOLOGICAL MEDIUM

The invention relates to a method for optical detection of analyte molecules in a natural biological medium.

The optical detection of individual molecules was first described in Applied Optics, Volume 15 (1976) page 2965. In the following years this detection technology was improved up to the detection of individual fluorophores, i.e. individual fluorescent chemical groups (Chemical Physics Letters, Volume 174 (1990) page 553).

However, it has not hitherto been possible to detect individual molecules in natural biological mediums. Such mediums when excited with light show a strong background luminescence (Analytical Chemistry Volume 68 (1996) page 2270). The luminescence results from the fact that buffer substances, enzymes and other macromolecules are contained in natural biological mediums. This luminescence is particularly strong in the case of blood plasma with its approximately 100 different proteins.

The object of the invention is to provide a method with which individual or a few analyte molecules can be detected in a natural biological medium.

In order to achieve this object the generic method is characterized in that
 the analyte molecules are marked with at least one fluorescent dye;
 that from an observed volume single photons are absorbed in the natural biological medium in order to carry out a time-correlated single photon count and to obtain time data for the single photons;
 that at least two patterns are predetermined, wherein a first pattern describes time data expected from the at least one fluorescent dye and a second pattern describes time data expected from the natural biological medium;
 that a comparative model is formed by a weighted addition of the patterns;
 that the comparative model is adapted to the obtained time data by variation of the weighting factors;
 that the values of the weighting factors for optimum conformity of the comparative model with the obtained time data are determined; and
 that the presence of at least one analyte molecule is assumed when the determined value of the weighting factor for the first pattern exceeds a predetermined threshold.

The marking of the analyte molecules with fluorescent dyes makes even non-fluorescent analyte molecules detectable.

The time data obtained by time-correlated single photon counts can be represented in the form of a decay curve for each predetermined time interval. The decay curve shows the progress of the fluorescence decay or respectively of the decay over time of the luminescence of a specimen located in the observed volume. As a rule the natural biological medium has a short luminescence decay time. For undiluted blood plasma the decay time in the case of excitation with light having a wavelength of 637 nm (1 nm=1 nanometer= $10^{-9}$ m) and detection of the photons in the wavelength range from 650 to 700 nm amounts to approximately 300 ps (1 ps=1 picosecond=$10^{-12}$ sec). If fluorescent dyes having a substantially longer fluorescent lifetime, e.g. 4 ns (1 ns=1 nanosecond=$10^{-9}$ sec), are chosen for the marking, then it is possible to establish how greatly the fluorescent dyes have contributed to the decay curve.

This can be achieved mathematically by the addition of known decay curves, so-called patterns, for the background luminescence of the natural biological medium and the fluorescent dyes used for marking, after multiplication by weighting factors. From this a comparative model is obtained. The weighting factors are then varied, and the values of the weighting factors for optimum conformity of the comparative model with the obtained time data are determined.

The values for the weighting factors which are obtained after optimization give information as to how great the amount of photons emanating from the fluorescent dyes is relative to the detected photons. If this amount is large or if it exceeds a predetermined threshold, then there is a high probability that single or in any case a few analyte molecules are present in the observed volume.

The method according to the invention therefore facilitates a high discrimination between the fluorescence of the fluorescent dyes and the background luminescence of the natural biological medium. With the aid of the method according to the invention it is possible, against a background of approximately 20,000 photons per second, to discriminate the approximately 100 photons which emanate from a marked analyte molecule and can be detected as the analyte molecule passes through the observed volume. This discrimination is a prerequisite for the reproducible detection of individual analyte molecules in the natural biological medium.

A further development of the invention utilizes the fact that the background luminescence of natural biological mediums, and particularly that of blood plasma, noticeably decreases when excitation light with a wavelength greater than 600 nm is used for the time-correlated single photon count. The wavelengths between 630 and 670 nm are particularly suitable for this. Since the fluorescence of the dyes is always red-shifted, a wavelength range used for the detection will always be of longer wavelength than the wavelength of the excitation. If photons are preferably detected which have a wavelength between 10 and 60 um longer than the respective excitation wavelength, then a preferred detection of the photons of the fluorescent dye and an improved discrimination between background and desired signal for the detection of individual analyte molecules is achieved.

A pulsed light source, an optical measuring arrangement and a detector, connected to an electronic detection arrangement, are used in the usual way for the time-correlated single photon counts in order to be able to detect the time gap between the time of detection of a photon and the time of the excitation pulse. In a preferred further development of the invention a diode laser is used as source for the excitation light. Diode lasers are very economical, very small and generate light at the desired wavelengths in the range from 630 to 670 nm.

In an advantageous further development of the invention a natural biological medium is examined with a number of analyte molecules. The different analyte molecules are specifically marked with different fluorescent dues each having different fluorescence decay behavior, e.g. difference fluorescent lifetimes.

In the case of mono-exponential fluorescent decay curves the decay curves for predetermined time intervals are modeled in such a way that the fluorescent lifetime is treated as an additional variable to be adapted. If the detected time data are described by such a model and if the values for the weighting factors and the fluorescent lifetimes are determined by adaptation, then on the one hand the weighting factors make it possible to determine whether a single or a few analyte molecules is/are present in the observed volume. However, the determination of the optimally appropriate fluorescent lifetime also makes it possible to make a statement as to the type of fluorescent dye used. In particular in this case it is possible to establish which of a plurality of different fluorescent dyes used for marking has been detected. This permits an identification of the analyte molecules specifically coupled to the dyes.

The invention is explained in greater detail below in relation to embodiments with reference to the drawings, in which:

FIG. 4A shows a curve which represents the number of photons detected in 10 ms units of time as a function of the time;

FIG. 4B shows a curve which represents the relative amount of photons attributable to fluorescence of the fluorescent dyes per unit of time for the time data on which FIG. 4A is based.

Figure 1:
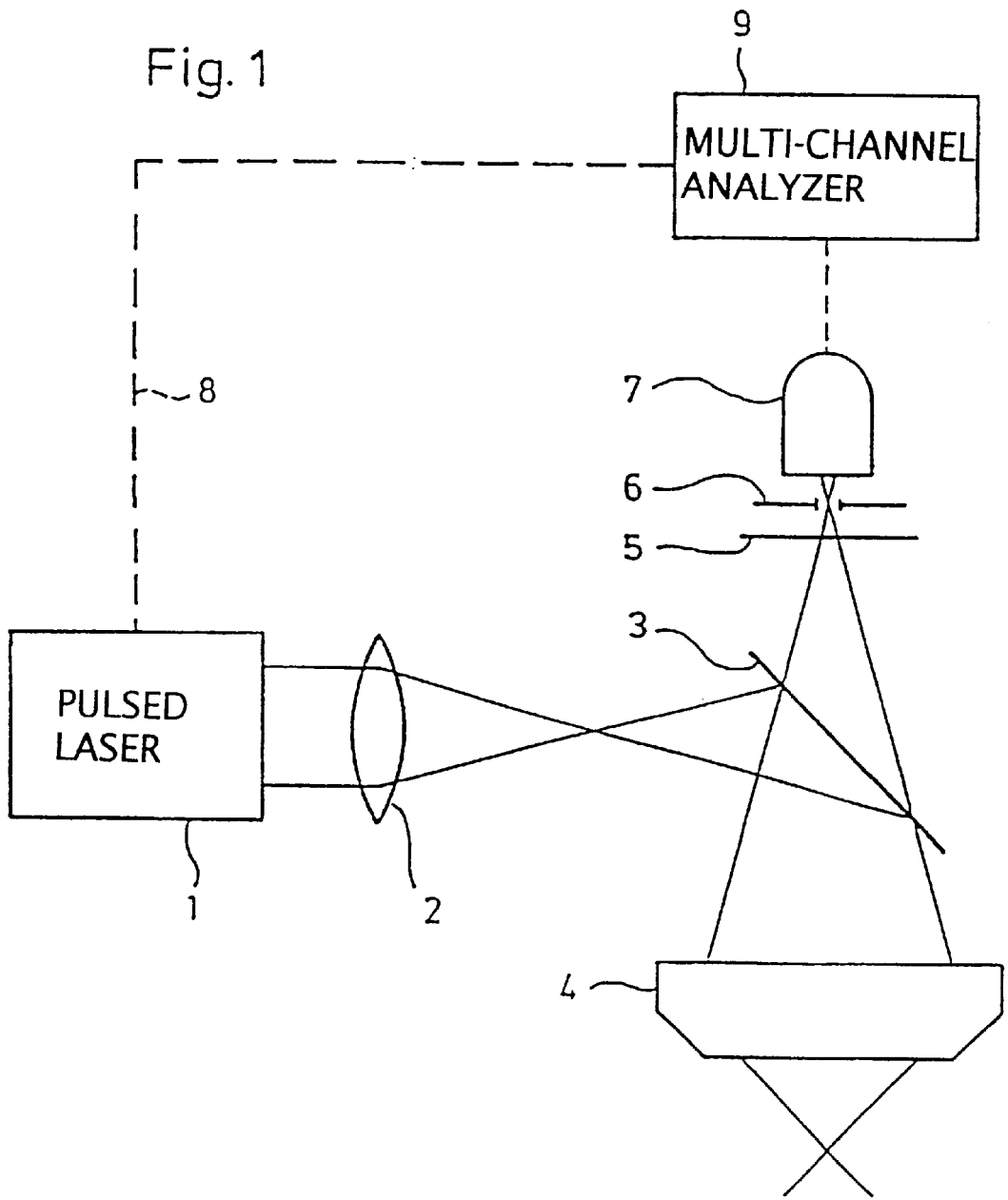
FIG. 1 shows a diagrammatic representation of an arrangement for time-correlated single photon counts.

The natural biological mediums under consideration are in particular tissue samples and undiluted blood plasma or blood serum. The mediums are examined without prior cleansing steps, which is why they are designated as "natural". In the following embodiments undiluted blood plasma is considered by way of example as natural biological medium.

The analyte molecules to be detected are in particular biomolecules, such as nucleic acids, proteins, peptides, hormones, porphyrins and antibodies, but also antigens, haptens and tumor markers, as well as toxic substances, environmental toxins, pesticides or pharmaceutical active substances such as alkaloids. In the following embodiments tumor markers are always considered as analyte molecules.

As a rule tumor markers are only capable of weak fluorescence. In order to be able to detect them they are marked with fluorescent dyes.

When excited by light, undiluted blood plasma shows a strong luminescence with wavelengths above 700 nm. In order nevertheless to be able to detect individual tumor markers in undiluted blood plasma, different measures must be taken in order to make this background recede. One of these measures consists of using light with a wavelength greater than 600 nm for the excitation. Furthermore, only light with a wavelength in the range below 700 nm, particularly between 650 and 700 nm, is detectable. This first measure alone already achieves a marked reduction in the background luminescence of the undiluted blood plasma.

Furthermore, the tumor markers are marked with dyes which have a high quantum yield of fluorescence. These dyes must absorb at the excitation wavelengths above 600 nm. Fluorescent dyes are particularly advantageous which have an absorption maximum in the range from 620 to 670 nm, a fluorescence red-shifted by 10 to 60 nm and a quantum yield of fluorescence of more than 10%. Such fluorescent dyes are described in the patent specifications DE 42 10 970 and W093/10189. One of the dyes described and used here bears the designation JA169. The commercially obtainable dye Cy5 is also suitable. In the described embodiment these two dyes are used for marking of the tumor markers.

Apart from the described spectral properties, when excited by light of 637 mn and when photons are detected in the wavelength range from 650 to 700 nm undiluted blood plasma shows a luminescence decay time of approximately 300 ps. In order to make a clear distinction between the background luminescence of undiluted blood plasma and the fluorescence of the marked tumor markers or dye, therefore, the dyes used for the marking should have fluorescent lifetimes which are clearly distinguished from the said 300 ps of the undiluted blood plasma. The aforementioned dyes Cy5 and JA169 have fluorescent lifetimes of 1.7 ns and 2.7 ns respectively. These fluorescent lifetimes are adequately distinguished from the said 300 ps. For this reason also the two said dyes are particularly suitable for the detection of individual tumor markers in undiluted blood plasma.

With the aid of the method according to the invention the differences in lifetime are used for further discrimination between the background signal and the fluorescence signal of the marked tumor markers.

In the embodiment under consideration the tumor markers to be detected are marked in the following way. Monoclonal antibodies appropriate to the tumor markers are added to the blood plasma. Dye molecules are coupled to the monoclonal antibodies, i.e. the monoclonal antibodies are marked for example with Cy5 or JA169. The monoclonal antibodies are capable of bonding selectively to the tumor markers and not to the other proteins in the blood plasma via an antibody-antigen reaction. In this way the dye molecules are also coupled to the tumor markers and thus the tumor markers are marked with fluorescent dyes.

For optical detection of the tumor markers a measurement is carried out using the technique of time-correlated single photon counting in an observed volume of blood plasma in which the marked tumor markers are dissolved.

Modulated light sources serve as light source for the excitation. Pulsed laser systems which deliver pulses with a pulse length less than 1 ns at a repetition rate of more than 10 MHz are particularly suitable. In this case the excitation lasers can be solid state lasers, dye lasers, ion lasers, gas lasers, but preferably diode lasers.

The use of pulsed light sources facilitates inter alia a separation between undelayed scattered light from the natural biological medium and the delayed fluorescent light of the dyes.

The diode lasers which are preferably used emit in the desired wavelength range above 600 nm. Typical wavelengths for diode lasers lie between 620 and 670 nm. The diode laser used here emits at a wavelength of 637 nm. Its pulse length is below 500 ps and its repetition rate is 30 MHz. Its mean power is 0.5 mW.

Reference is made in the following to FIG. 1. The light beam of the diode laser 1 is input into a microscope objective 4 by way of a lens 2 and a dichroic beam splitter 3. The microscope objective has a strong magnification and a high numerical aperture. With the aid of the microscope objective the laser beam is focused into the observed volume.

The focusing of the laser beam limits the observed volume to a few femtoliters. With a concentration of $10^{-9}$ or fewer mols of tumor marker per liter of blood plasma, on average there is less than one tumor marker in the observed volume.

The probability that more than one tumor marker is present in the observed volume is correspondingly less.

The time which a tumor marker molecule requires in order to diffuse through the observed volume, i.e. the residence time or measurement time, is between fractions of 1 ms and a few ms. While the fluorescence-marked tumor marker is present in the observed volume the fluorescent dye coupled on the tumor marker can absorb light as a functions of its extinction coefficient at the excitation wavelength. The absorbed light is emitted again in the form of photons as a function of the quantum yield of fluorescence and the fluorescent lifetime, the triple yield and lifetime and the photostability of the fluorescent dyes. During the measurement time the fluorescent dyes go through several such excitation and emission cycles.

The emitted photons are collected again with the aid of the microscope objective 4.

The photons emitted by the fluorescent dyes and collected by the microscope objective pass through the dichroic beam splitter 3, which is constructed in such a way that it transmits the red-shifted fluorescent light. Behind the dichroic beam splitter is located a spectral filter 5, generally an interference filter, which is constructed in such a way that it transmits the emission wavelength of the fluorescent dyes as free as possible of losses and as far as possible blocks all other wavelengths. With the aid of the dichroic beam splitter and the interference filter the spectral separation of the luminescence of the blood plasma and of the scattered light from the fluorescence of the dyes which is not shifted in the wavelength results in a further reduction in the unwanted background luminescence and thus an improvement in the discrimination between the signal of the fluorescence-marked tumor markers and the blood plasma.

Behind the spectral filter is located a diaphragm 6 with a diameter of 50 to 200 $\mu$m, preferably with a diameter of 100 $\mu$m. The observed volume is imaged onto this diaphragm. This results in a spatial restriction of the observed volume to the focus of the laser beam in the blood plasma. Such an arrangement is designated as a confocal microscope for reflected light or for epifluorescence.

A detector 7 is located behind the diaphragm 6. The detector must be so constructed that it can detect individual photons with high temporal resolution. Photomultipliers and avalanche photodiodes are suitable for this. Avalanche photodiodes based on silicon semiconductors are particularly suitable for the detection of photons at wavelengths between 650 and 700 nm. The quantum efficiency of these avalanche photodiodes in the said spectral range between 650 and 700 nm is up to 70%. Furthermore avalanche photodiodes have a very low dark counting rate of below 60 pulses per second. Therefore they are very sensitive with very low background noise.

With the means 8 which are usual for time-correlated single photon counts the time gap between the time of the excitation of the fluorescent dyes by a pulse of the diode laser 1 and the time of the detection of a photon, on the avalanche photodiode 7 is determined. For each detected photon the time data thus determined is sorted with the aid of a multi-channel analyzer 9 into a time slot.

This sorting can take place both immediately and also not until a subsequent evaluation.

Since during the passage of the tumor markers through the observed volume the fluorescent dyes which are coupled to the tumor markers go through a plurality of excitation and emission cycles, as a tumor marker passes through the observed volume a shower of photons is produced which is detected by the detector. The number of photons which can be detected per passage of a tumor marker molecule through the observed volume is several 100. These photons can be collected in time intervals of for example 10 ms each.

As an alternative to this, in addition to the time gap between the time of excitation and of detection the absolute time of detection can be determined for each photon. The time data is then preferably added up in time intervals which have been adapted to the passage of a tumor marker molecule through the observed volume.

Figure 2:
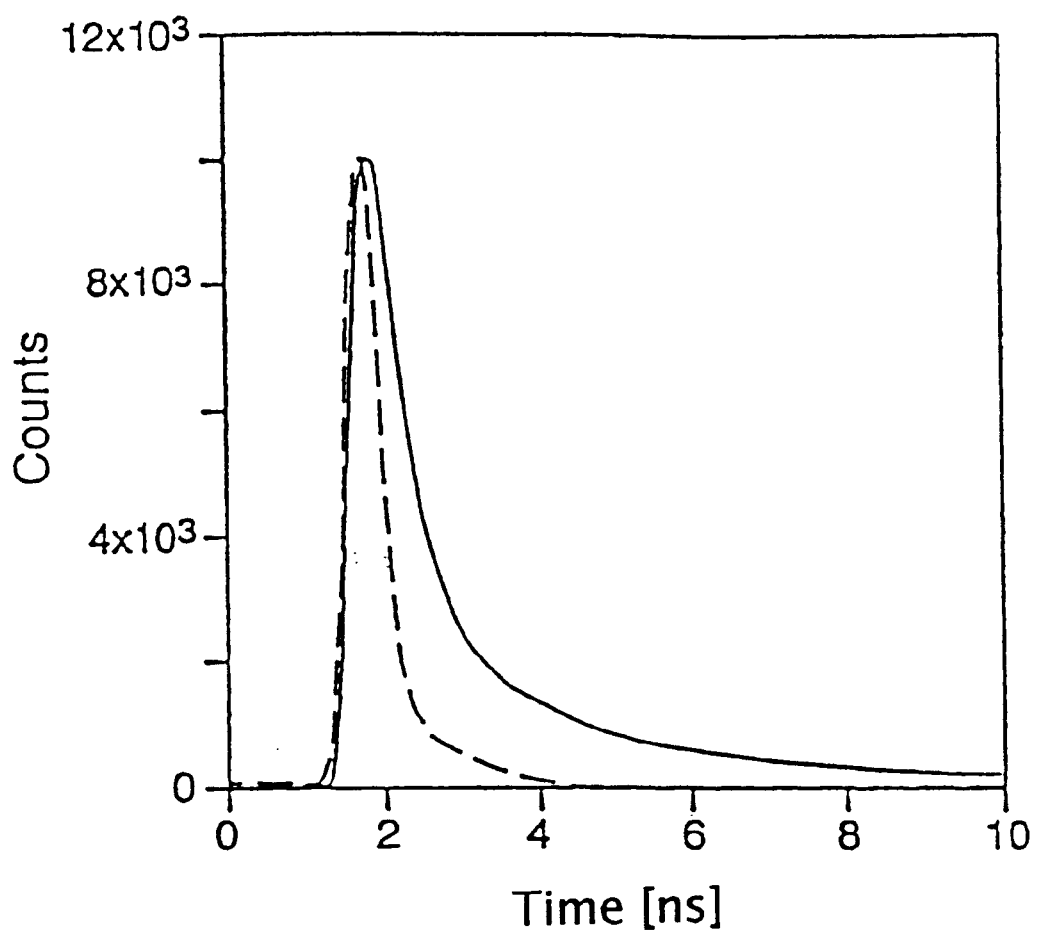
FIG. 2 shows a curve which represents the results of measurements by means of time-correlated single photon counts for undelayed scattered light (broken line) and for undiluted blood plasma (solid line)

In FIG. 2 the time gap between the excitation by an excitation pulse of the laser 1 and the time of detection of a photon by the detector 7 is plotted on the x-axis. The number of detection events, designated here as "counts", sorted into a time slot are plotted on the y-axis. The width of a typical time slot is 50 ps.

In FIG. 2 the broken line shows a decay curve recorded by time-correlated single photon counts with the described arrangement for a solution which scatters the excitation light without a delay. This so-called instrument function reflects the maximum temporal resolution which results from the width of the excitation pulses and the temporal resolving power of the detector 7 and the connected apparatus 9. Each recorded decay curve, e.g. of the fluorescent dyes, cannot be observed in its possibly pure exponential configuration but is always observed as the result of a convolution with the instrument function. A reconstruction of the pure exponential decay function is possible by a deconvolution of the measured decay curve.

In FIG. 2 the solid line shows a decay curve for blood plasma which is measured by time-correlated single photon counts with the described arrangement. In the case of excitation by light at 637 nm and detection of the photons in the range from 650 to 700 nm, the decay curve of the blood plasma shows a decay time of approximately 300 ps.

Figure 3:
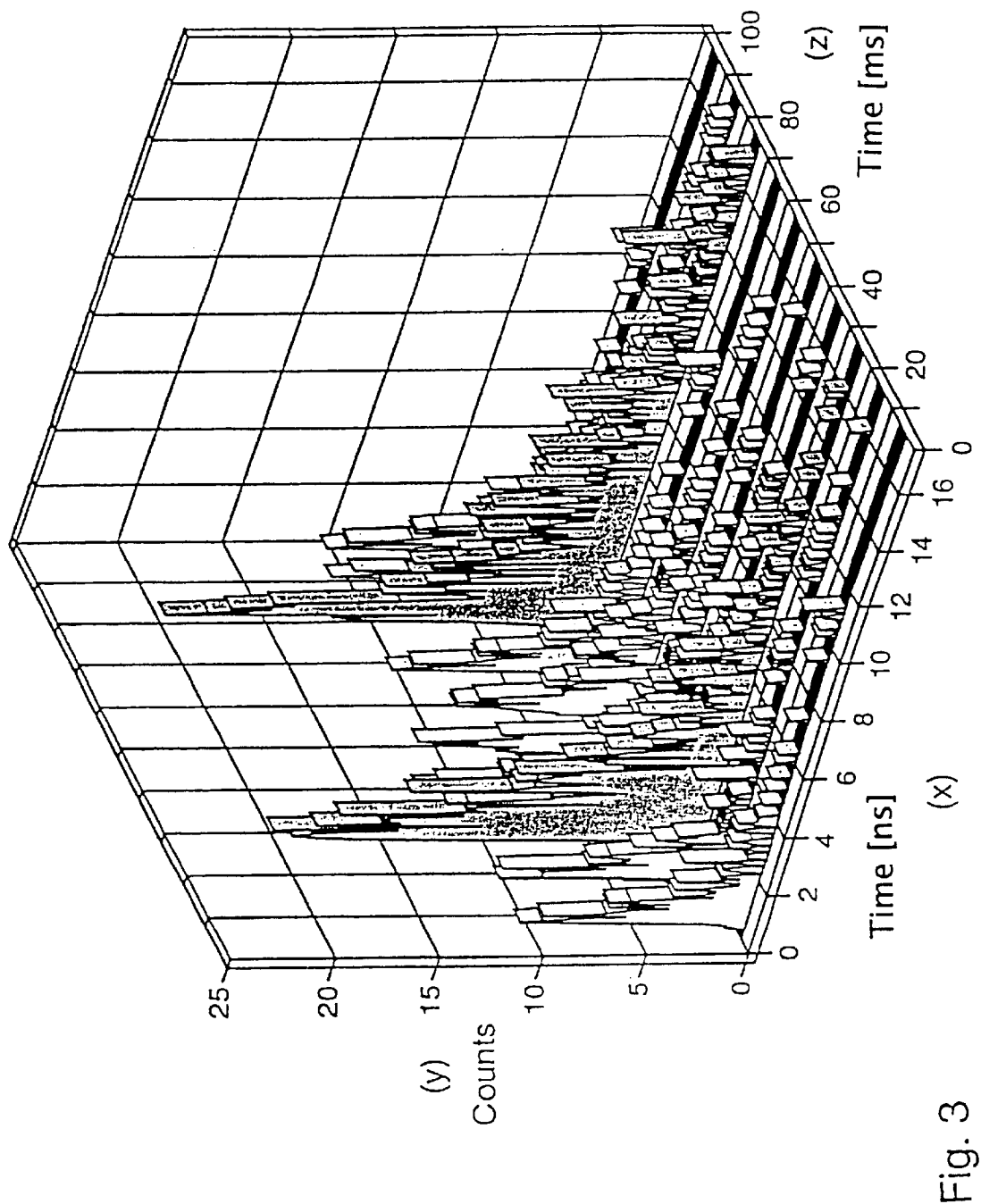
FIG. 3 shows histograms of measurements by means of time-correlated single photon counts on an undiluted blood plasma specimen containing differently marked antibodies.

As in FIG. 2, in FIG. 3 again the time gap in ns between the excitation pulse and the detection of a photon is plotted on the x-axis and the counts are plotted on the y-axis, whilst the time elapsed during the measurement is plotted in ms on the z-axis. The time data obtained were added up for each 10 ms and represented as a decay curve. As mentioned, the blood plasma contains for example two differently marked antibodies in a concentration of $10^{-11}$ mols per liter. Whilst the first 20 ms in FIG. 3 show the pure background luminescence of the blood plasma sample, after approximately 30 ms a Cy5 marked antibody migrates into the observed volume. After 80 ms a JA169 marked antibody migrates into the observed volume.

It will be seen that in FIG. 3 the decay curves of the blood plasma, of the Cy5 marked antibody and of the JA169 marked antibody differ in particularly in that the characteristic decay time is a different length. The decay time of JA169 is 2.7 ns and can be clearly recognized as the longest of the three decay times under consideration.

Figures 4, 4A, 4B:
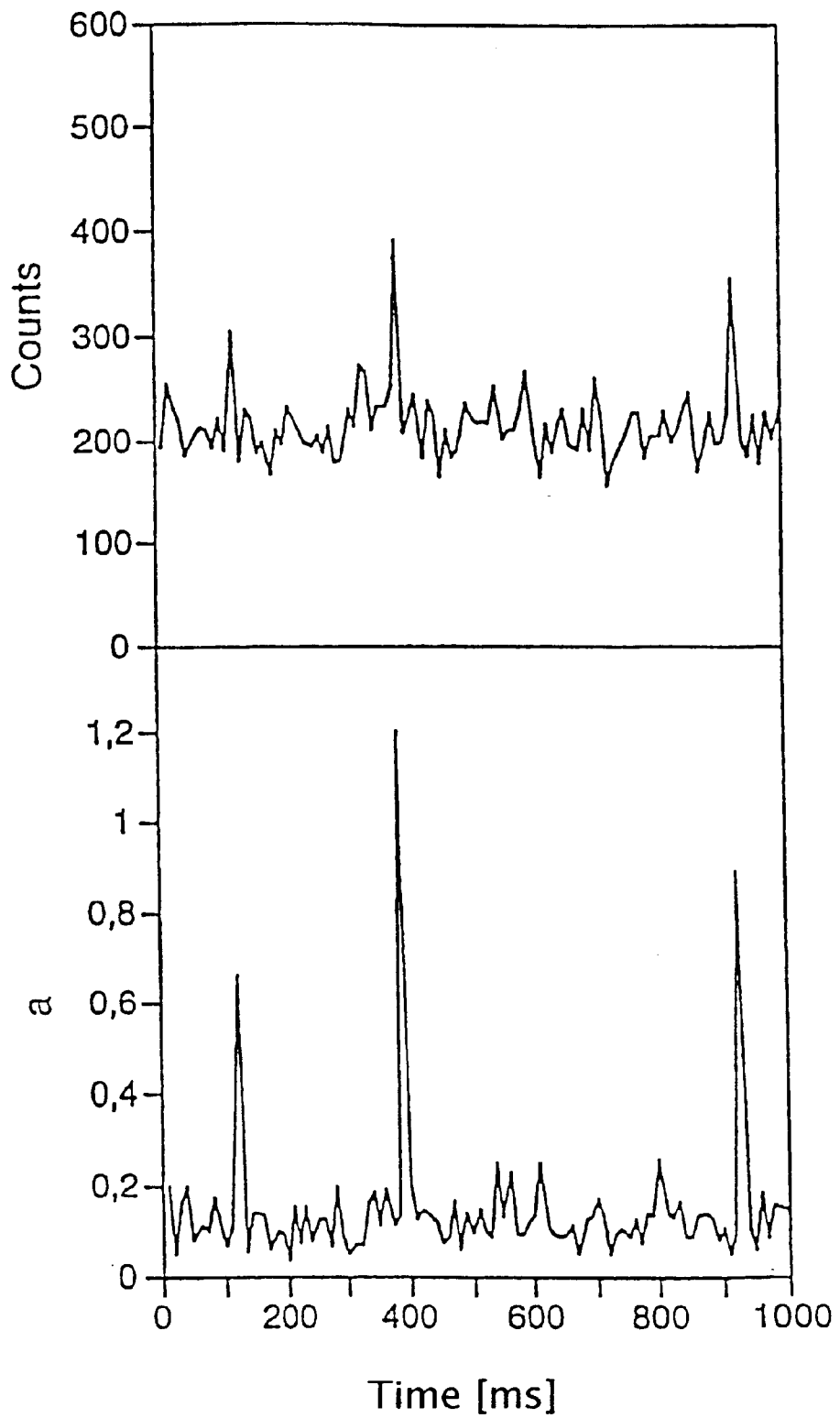

FIG. 4A shows the number of photons detected per unit of time of 10 ms (counts or counting rate) as a function of the time in ms elapsed during the measurement. Out of the pure blood plasma approximately 200 photons per 10 ms are detected. During the passage of a dye-marked tumor marker molecule the counting rate increases, as can be seen in FIG. 4A at approximately 400 and approximately 900 ms.

It is described below how a reliable detection of individual dye-marked tumor marker molecules can be achieved.

In order to be able to conclude from the decay curves obtained for predetermined time intervals whether in the time interval under consideration an analyte molecule, in this case a tumor marker, was present in the observed volume, the method described below can be preceded by a step in which the decay curves are deconvoluted with the aid of the instrument functions. Thus everything which follows can relate either to deconvoluted decay curves or to non-deconvoluted decay curves.

First of all at least two patterns are predetermined, wherein a first pattern reproduces the expected progress of the decay curve for the fluorescent dyes used for the marking and a second pattern reproduces the expected progress over time of the decay curve for the background luminescence of the natural biological medium, that is to say in this case the undiluted blood plasma. In the following the pattern for the fluorescent dyes is designated as $p_1(i)$ and the pattern for the undiluted blood plasma is designated as $p_2(i)$. In this case i denotes the i-th microscopic time interval, i.e. the time slots for example 50 ps wide of the x-axis of the representation of the decay curves according to FIG. 2.

The patterns can not only be obtained directly from calibrated measurements but also they can be produced on the basis of the data obtained by calibrated measurements. In the first case the patterns will be a concrete predetermined amount of numbers which are obtained from the calibrated measurements, optionally after smoothing and standardizing to 1. In the second case the patterns are obtained with the aid of a mathematical function, e.g. an exponential drop, from which concrete values for the $p_1(i)$ or $p_2(i)$ can be calculated.

The patterns are advantageously standardized to one, i.e.

$$\sum_i p_1(i) = 1 \text{ and } \sum_i p_2(i) = 1 \qquad (1)$$

addition being carried out over all microscopic time slots i.

In order to obtain a model which can be compared with the obtained decay curves, the predetermined patterns $p_1(i)$ and $p_2(i)$ are weighted and added, i.e. added after they have been multiplied by weighting factors $A_1$ and $A_2$:

$$P(i)=A_1 p_1(i)+A_2 p_2(i) \qquad (2)$$

Thus p(i) is the model which is compared with the obtained decay curves.

In an adaptation test the comparative model can be adapted to the obtained decay curves by variation of the weighting factors $A_1$ and $A_2$.

Suitable adaptation tests are in particular the test of the least square deviation and an information theory test which is based on the minimal Kullback-Leibler discrimination data as gap measurement. The former is simpler to handle, and the latter has a particularly low statistical error rate.

The values of the weighting factors for optimal conformity of the comparative model with the obtained decay curves can be obtained by an adaptation test. The presence of at least one tumor marker is assumed when the weighting factor $A_1$ exceeds a predetermined threshold. This threshold must be predetermined as a function of the concrete experimental conditions and the desired certainty of detection.

The pattern p(i) is preferably expressed by a standardized form of the weighting factors:

$$P(i)=N(a p_1(i)+(1-a)p_2(i)) \qquad (3)$$

in which case $$A = \frac{A_1}{A_1 + A_2} \text{ and } N = A_1 + A_2 \qquad (4)$$

Thus a gives the relative amount of detected photons which can be attributed to fluorescence of the fluorescent dyes. N is the total number of detected photons which were used to produce the obtained decay functions. If as in the present embodiment the decay curve is produced in each case for a time interval of 10 ms, then N represents the number of photons detected in the predetermined time interval of 10 ms.

Thus the pattern $p_1(i)$ represented in this way is automatically standardized in its total amplitude to the total number of photons detected in the predetermined time interval, as is clear from equation (5) using equation (3) and equation (1):

$$\sum_i p(i) = N\left(a \sum_i p_1(i) + (1-a) \sum_i p_2(i)\right) \qquad (5)$$
$$= N(a \cdot 1 + (1-a) \cdot 1) = N$$

This model is adapted to the obtained decay curve by variation of the relative amount a. In this way the value for the relative amount a is determined for optimal conformity of the comparative model thus represented with the obtained decay curve. If the relative amount a exceeds a predetermined threshold then the presence of at least one tumor marker in the observed volume is assumed. A threshold of 0.3 has proved suitable.

A dye-marked antibody bonded to the tumor marker can be distinguished from an unbonded dye-marked antibody for example with the aid of the residence time in the observed volume.

Likewise the diffusion constant of the detected molecule can be ascertained in a known manner by way of a correlation function. In this case an increase in the diffusion constant points to a bonded state of the marked antibody and thus to the detection of a tumor marker molecule.

Furthermore, the bonding of antibodies marked with dyes on analyte molecules or tumor markers can be established in the following manner.

The antibodies are marked with two different dye molecules. In this case the dye molecules differ in their fluorescent lifetime. The first dye should have a fluorescent lifetime of $\tau_{11}$ and the second $\tau_{12}$.

As a rule antigens, that is to say in this case the tumor markers, have more than one bonding point for antibodies. Approximately 100 antibodies are sometimes bonded to an antigen. The bonding of more than one dye-marked antibody onto a tumor marker produces a complex of tumor markers and more than one dye-marked antibody. The more dye-marked antibodies are bonded on the tumor marker, the higher is the probability that the two different dyes are present in the complex.

The bonding of the dye-marked antibodies onto a tumor marker and thus the presence of a tumor marker can then be established if not only due molecules with the fluorescent lifetime $\tau_{11}$ but also those with $\tau_{12}$ are detected simultaneously in the observed volume. There is a high probability that unbonded dye-marked antibodies are present singly in the observed volume and not simultaneously with other dye-marked antibodies.

This can be quantified mathematically in that a superimposition of the decay curves for both fluorescent lifetimes $\tau_{11}$ and $\tau_{12}$ is predetermined as the first pattern, i.e. the pattern for the fluorescence decay curve of the dyes. The relative amounts of the individual lifetimes on the first pattern could amount for example to 50% in this case. In order to have a quantitative criterion for the presence of a complex in the observed volume, the relative amount a associated with the first pattern is then considered again. If it exceeds the value of 0.3, then there is a high probability that a tumor marker is present in the observed volume.

Likewise for the quantitative determination the comparative model can be built up from three patterns, a first one corresponding to a fluorescence decay curve with the fluorescent lifetime $\tau_{11}$, the said second pattern for the blood plasma and a third pattern corresponding to a fluorescence decay curve with the fluorescent lifetime $\tau_{12}$. Then both the relative amount for $\tau_{11}$ and that for $\tau_{12}$ are determined. A criterion for the presence of a tumor marker in the observed volume is then, for example, that the sum of the relative amounts for $\tau_{11}$ and $\tau_{12}$ is greater than 0.3 and additionally each individual relative amount is greater than 0.1.

With this method the antibody molecules can also be marked with more than two different dye molecules, for which corresponding patterns and comparative models are predetermined.

Apart from the use of calibrated measurements, the patterns $p_1(i)$ and $p_2(i)$ can also be described, as mentioned above, by suitable mathematical models which are built up from data obtained in calibrated measurements. Typically it will be observed that the fluorescence of fluorescent dyes can be described by a mono-exponential pattern. Thus the patterns $p_1(i)$ and $p_2(i)$ can be described in deconvoluted form by equation (6):

$$p_1(i) = \Delta t(i) \frac{1}{\tau_1} e^{-t(i)/\tau_1} \tag{6}$$

so long as $\Delta t(i)$ can be assumed to be small relative to the fluorescent lifetime $\tau_1$. In this case $\Delta t(i)$ is the duration of a microscopic time interval, 50 ps in the embodiment under consideration, and $\tau_1$ is the fluorescent lifetime of the fluorescent dyes used for marking the tumor marker molecules. For Cy5 $\tau_1$ is 1.7 ns and for JA169 it is 2.7 ns. T(i) is the microscopic point in time at which the i-th microscopic time interval begins.

As a rule all microscopic time intervals $\Delta t(i)$ have the same time duration $\Delta t$ so that $$\Delta t(i) = \Delta t$$

and $$t(i) = i\Delta t \tag{7}$$

If the microscopic time intervals or time slots i are not counted from slot 0 but from slot 1, then as appropriate i must be replaced by (i−1).

Under these conditions the following is obtained as a pattern for a mono-exponential decay:

$$p_1(i) = \Delta t \frac{1}{\tau_1} e^{-i\Delta t/\tau_1} \tag{8}$$

The pattern p1(i), as represented in equation (6) or (8) can be used to be added with weighting to a deconvoluted pattern $p_2(i)$ obtained from a calibrated measurement. The model obtained by this weighted addition can then be compared with the obtained deconvoluted decay curves in order to obtain the relative amount a.

Likewise the pattern $p_1(i)$ obtained by equation (6) or (8) can be convoluted with the instrument functions. After this it can be weighted and added to a non-deconvoluted pattern $p_2(i)$ obtained from a calibrated measurement. The resulting p(i) can be compared with a non-deconvoluted obtained decay curve.

Likewise the decay curve for the undiluted blood plasma can be described by a mono-exponential decay according to equation (9):

$$p_2(i) = \Delta t \frac{1}{\tau_2} e^{-i\Delta t/\tau_2} \tag{9}$$

wherein $\tau_2$ is the effective luminescence decay time of the undiluted blood plasma which amounts to approximately 300 ps in the case of excitation by light at 637 nm and detection of the photons in the range from 650 to 700 nm.

If both patterns $p_1(i)$ and $p_2(i)$ are described by mono-exponential shapes of the decay curves, then this is referred to as a bi-exponential model.

FIG. 4B shows the relative amount a determined during a measurement for various time intervals of 10 ms each. If FIGS. 4A and 4B are compared, then it will be seen that a consideration of the relative amount a effects a marked improvement in the signal-to-noise ratio relative to FIG. 4A. Furthermore, it will be additionally noted in FIG. 4B that at approximately 100 ms a further tumor marker passed through the observed volume. This could not be reliably recognized in FIG. 4A. In FIG. 4A only the number of photons detected per 10 ms was considered. The consideration of the relative amount a is possible due to the fact that the individual photons are detected in a time-correlated manner and thus the data contained in the different decay times can be used.

A second embodiment is described below which in addition to the detection of individual tumor marker molecules also permits an identification of different tumor markers or analyte molecules. Thus an undiluted blood plasma is examined in which various tumor markers are dissolved.

In this second embodiment the various tumor markers to be detected are marked in the following way. Various monoclonal antibodies appropriate to the various tumor markers are added to the blood plasma. Various dye molecules are in each case coupled to the monoclonal antibodies. One monoclonal antibody is marked for example with Cy5 and another with JA169. Such marking can take place during preparation of the monoclonal antibodies.

The fluorescent dyes chosen for the specific marking must in each show a different fluorescence decay behavior, since this is used for the identification.

The various monoclonal antibodies are capable, as described, of bonding onto the various tumor markers by way of an antibody-antigen reaction. In this way the various dye molecules are also coupled specifically to the tumor markers.

In FIG. 3 it can be seen that the antibody molecule which is located in the observed volume at 30 ms is marked with Cy5, whilst the antibody molecule which is located in the observed volume at 80 ms is marked with JA169, since the decay curve at 30 ms drops faster than the one at 80 ms, that is to say it as a shorter fluorescent lifetime. Thus in principle the tumor markers are identifiable on the basis of the fluorescent lifetime of the fluorescent dyes specifically linked to them.

For identification of the various tumor markers by way of the differing fluorescence decay behavior of the dyes a first pattern is predetermined for each dye used for marking. Then for each dye this pattern is weighted and added to the predetermined second pattern for the blood plasma in order to obtain associated comparative models in each case. The conformity between the respective comparative model and the obtained time data is optimized by variation of the weighting factors.

The comparative model which has the best conformity with the obtained time data is regarded as the applicable comparative model. The first pattern of a dye used in order to produce this comparative model gives information concerning the presence of this dye in the observed volume. This in turn—because of the specific marking of the tumor markers—gives information as to which tumor marker has been detected.

In a further development of the second embodiment the various fluorescent dyes are chosen so that they allow a mono-exponential development of the fluorescence over time to be expected. The first pattern $p_1(i)$ is described by equation (6) or (8). The fluorescent lifetime $\tau_1$ is used as additional variable for adaptation of the comparative pattern to the obtained decay curve.

Thus on the one hand the relative amount a and on the other hand the optimally appropriate fluorescent lifetime cl are obtained as the result of an adaptation between the comparative model and the obtained decay curve. The relative amount a facilitates the detection of the tumor marker molecules, whilst the obtained fluorescent lifetime $\tau_1$ permits their identification.

Not only patterns obtained by calibrated measurement but also patterns obtained from a mono-exponential model can be used in this embodiment as pattern $p_2(i)$ for blood plasma. In the latter case a luminescence decay time of 300 ps of the blood plasma is assumed.

Also in this embodiment the patterns or decay curves can be evaluated in deconvoluted or non-deconvoluted forms.

Figure 5:
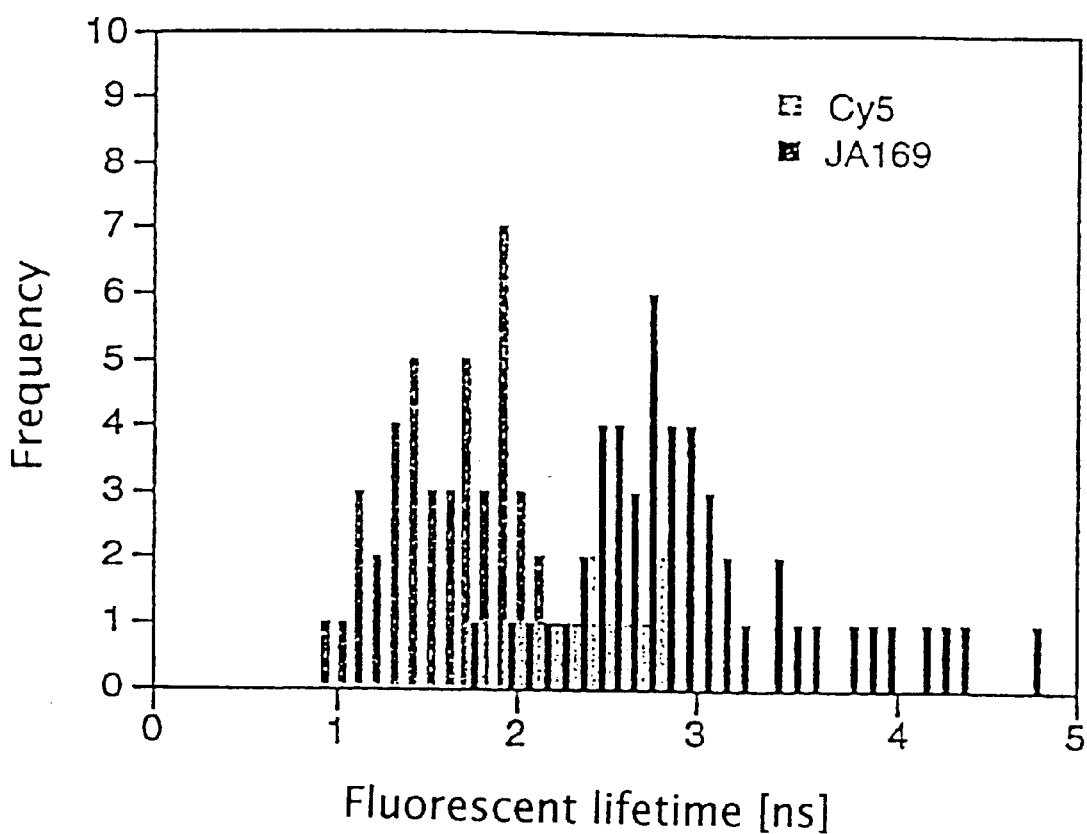
FIG. 5 shows a frequency distribution of certain fluorescent lifetimes for the dyes Cy5 and JA169.

FIG. 5 shows the frequency of fluorescent lifetimes in ns, as they have been determined with the aid of the method just described for the dyes Cy5 and JA 169 used for marking. It will be seen that the fluorescent lifetimes determined for Cy5 and JA169 are centered around a mean value of 1.7 and 2.7 ns respectively and can be recognized with sufficient reliability.

If in a third embodiment the comparative pattern is described by the simple equation (10):

$$p(i) = B_1 e^{-t(i)/\tau_1} + B_2 e^{-t(i)/\tau_2} \qquad (10)$$

then a comparison with equations (3), (6) and (8) shows that:

$$B_1 = Na\frac{\Delta t}{\tau_1} \text{ and } B_2 = N(1-a)\Delta\frac{t}{\tau_2} \qquad (11)$$

In this embodiment the criterion used for the presence of a tumor marker in the observed volume is the exceeding of a threshold by the standardized product of the weighting factor $B_1$ with the determined fluorescent lifetime $\tau_1$. This standardized product is defined as:

$$\frac{B_1 \tau_1}{B_1 \tau_1 + B_2 \tau_2} \qquad (12)$$

It will be seen from equation (13) with the aid of equation (11) that this standardized product is equal to the relative amount a:

$$\frac{B_1 \tau_1}{B_1 \tau_1 + B_2 \tau_2} = \frac{Na\Delta t}{Na\Delta t + N(1-a)\Delta t} = a \qquad (13)$$

Within the scope of the idea of the invention numerous variants are possible. For example it is not essential to combine the time data for predetermined time intervals into decay curves or to represent them as such. On the contrary, calculation can be made directly with the aid of corresponding mathematical models with the time data obtained for each detected photon. The patterns are formed appropriately in such a case and do not necessarily form decay curves.

Also for the patterns $p_1(i)$ and $p_2(i)$ non only mono-exponential models but also a multi-exponential or other model can be used. These models preferably do not contain any further variables. However, it is also conceivable that these models do contain firer variables, for instance the weights of individual exponential components.

Furthermore, apart from the mentioned dyes Cy5 and JA169 other dyes can also be used for marking.

Finally, apart from the described biochemical specific antibody-antigen reaction other, e.g. covalent routes could be taken for the marking or hybridization between DNA strands is utilized.

What is claimed is:

1. Method for optical detection of analyte molecules in a natural biological medium, characterized in that the analyte molecules are marked with at least one fluorescent dye;

that from an observed volume single photons are absorbed in the natural biological medium in order to carry out a time-correlated single photon count and to obtain time data for the single photons;

that at least two patterns are predetermined, wherein a first pattern describes time data expected from the at least one fluorescent dye and a second pattern describes time data expected from the natural biological medium;

that a comparative model is formed by a weighted addition of the patterns;

that the comparative model is adapted to the obtained time data by variation of the weighting factors;

that the values of the weighting factors for optimum conformity of the comparative model with the obtained time data are determined; and that the presence of at least one analyte molecule is assumed when the determined value of the weighting factor for the first pattern exceeds a predetermined threshold.

2. Method as claimed in claim 1, characterized in that for marking of the analyte molecules fluorescent dyes are used with a red shift between 10 and 60 nm;

that excitation light with a wavelength between 630 and 670 nm is used; and that the detection is concentrated on photons with a wavelength between 10 and 60 nm longer than the respective excitation light.

3. Method as claimed in claim 2, characterized in that a diode laser is used as light source (1) for the excitation light.

4. Method as claimed in one of claims 1 to 3, characterized in that in the case of examination of a natural biological medium with a plurality of different analyte molecules a) various fluorescent dyes each with different fluorescent lifetimes are used for specific marking of the various analyte molecules.

5. Method as claimed in claim 4, further characterized in that b) each of the various fluorescent dyes is chosen so that it allows a mono-exponential development of the fluorescence over time to be expected;

c) the first pattern is obtained from this development of fluorescence;

d) the value of the fluorescent lifetime for the first pattern is determined for optimized conformity of the comparative model with the obtained time data by variation of the first pattern as a function of the fluorescence; and that e) each analyte molecule is identified by means of the chosen fluorescent lifetime optimized in step d) for the first pattern.

* * * * *